US00PP33564P2

(12) United States Plant Patent
Wood

(10) Patent No.: US PP33,564 P2
(45) Date of Patent: Oct. 19, 2021

(54) ***CEPHALANTHUS* PLANT NAMED 'SMCBM'**

(50) Latin Name: *Cephalanthus occidentalis*
Varietal Denomination: SMCBM

(71) Applicant: Timothy D. Wood, Spring Lake, MI (US)

(72) Inventor: Timothy D. Wood, Spring Lake, MI (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 17/121,332

(22) Filed: Dec. 14, 2020

(51) Int. Cl.
*A01H 6/76* (2018.01)
*A01H 5/00* (2018.01)

(52) U.S. Cl.
USPC ..... Plt./226

(58) Field of Classification Search
USPC ..... Plt./226
See application file for complete search history.

*Primary Examiner* — Annette H Para
(74) *Attorney, Agent, or Firm* — C. Anne Whealy

(57) ABSTRACT

A new and distinct cultivar of *Cephalanthus* plant named 'SMCBM', characterized by its upright and mounded plant habit; moderately vigorous growth habit; freely branching habit; dense and bushy habit; glossy green-colored leaves becoming dark red in the autumn; spherical head-type inflorescences with numerous white-colored flowers; attractive medium red-colored fruits; and good garden performance and winter hardiness.

4 Drawing Sheets

Figure 1:
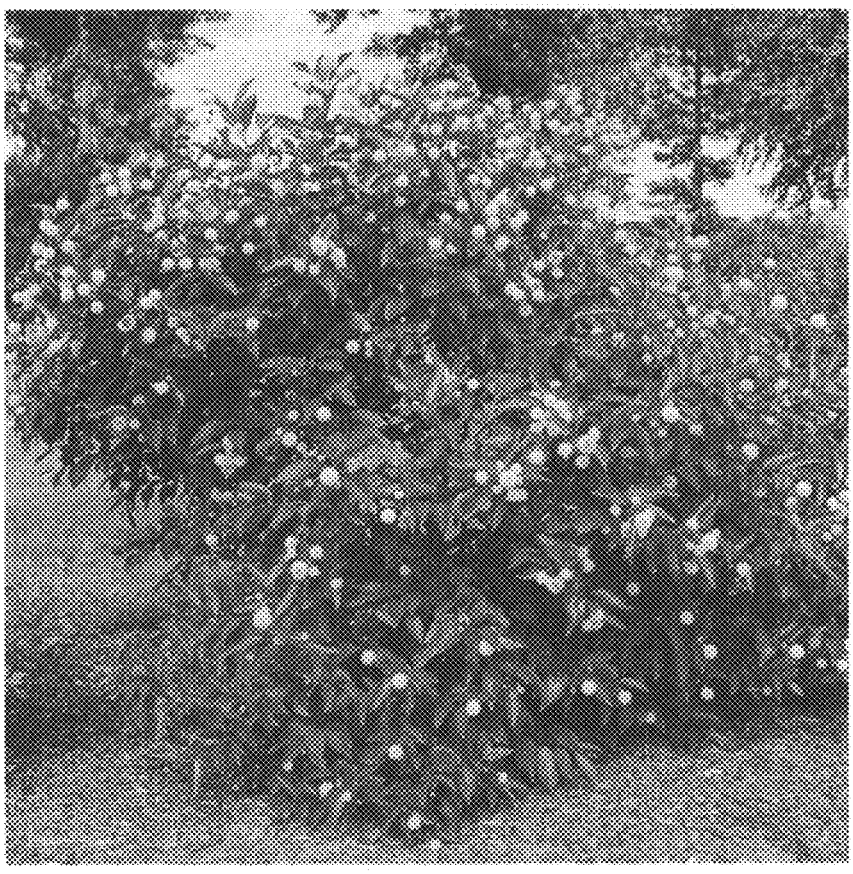

Botanical designation: *Cephalanthus occidentalis.*
Cultivar denomination: 'SMCBM'.

STATEMENT REGARDING PRIOR DISCLOSURES BY INVENTOR/APPLICANT & ASSIGNEE

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or the Assignee. Inventor/Applicant and Assignee claim a prior art exemption under 35 U.S.C. 102(b)(1) for disclosure and/or sales prior to the filing date but less than one year prior to the effective filing date.

BACKGROUND OF THE INVENTION

The present invention relates to a new and distinct *Cephalanthus* plant, botanically known as *Cephalanthus occidentalis* and hereinafter referred to by the name 'SMCBM'.

The new *Cephalanthus* plant is a product of a controlled breeding program conducted by the Inventor in Grand Haven, Mich. The objective of the breeding program is to create freely branching and freely flowering *Cephalanthus* plants with attractive summer and autumn leaf color, numerous attractive fruits and winter hardiness.

The new *Cephalanthus* plant originated from an open-pollination during the summer of 2010 in Grand Haven, Mich. of *Cephalanthus occidentalis* 'Sugar Shack', not patented, as the female, or seed, parent with an unknown selection of *Cephalanthus occidentalis* as the male, or pollen, parent. The new *Cephalanthus* plant was discovered and selected by the Inventor during the summer of 2015 as a single flowering plant within the progeny of the stated open-pollination in a controlled environment in Grand Haven, Mich.

Asexual reproduction of the new *Cephalanthus* plant by softwood cuttings in a controlled environment in Grand Haven, Mich. since the summer of 2015 has shown that the unique features of this new *Cephalanthus* plant are stable and reproduced true to type in successive generations of asexual reproduction.

SUMMARY OF THE INVENTION

Plants of the new *Cephalanthus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SMCBM'. These characteristics in combination distinguish 'SMCBM' as a new and distinct *Cephalanthus* plant:

1. Upright and mounded plant habit.
2. Moderately vigorous growth habit.
3. Freely branching habit; dense and bushy habit.
4. Glossy green-colored leaves becoming dark red in the autumn.
5. Spherical head-type inflorescences with numerous white-colored flowers.
6. Attractive medium red-colored fruits.
7. Good garden performance and winter hardiness.

Plants of the new *Cephalanthus* can be compared to plants of the female parent, 'Sugar Shack'. Plants of the new *Cephalanthus* differ from plants of 'Sugar Shack' in the following characteristics:

1. Plants of the new *Cephalanthus* are larger than and not as dwarf as plants of 'Sugar Shack'.

2. Leaves of plants of the new *Cephalanthus* are lighter green in color than leaves of plants of 'Sugar Shack'.
3. Plants of the new *Cephalanthus* and 'Sugar Shack' differ in fruit color as plants of the new *Cephalanthus* produce lighter red-colored fruits than plants of 'Sugar Shack'.

Plants of the new *Cephalanthus* can be compared to plants of the *Cephalanthus occidentalis* 'Magical Moonlight', not patented. In side-by-side comparisons, plants of the new *Cephalanthus* differ from plants of 'Magical Moonlight' in the following characteristics:

1. Plants of the new *Cephalanthus* are more upright than and not as mounding as plants of 'Magical Moonlight'.
2. In the autumn, leaves of plants of the new *Cephalanthus* become dark red in color whereas leaves of plants of 'Magical Moonlight' do not develop autumn color.
3. Plants of the new *Cephalanthus* and 'Magical Moonlight' differed in fruit color as plants of the new *Cephalanthus* produce medium red-colored fruits whereas plants of 'Magical Moonlight' produce yellow green-colored fruits.

BRIEF DESCRIPTION OF THE PHOTOGRAPHS

The accompanying colored photographs illustrate the overall appearance of the new *Cephalanthus* plant showing the colors as true as it is reasonably possible to obtain in colored reproductions of this type. Colors in the photographs may differ slightly from the color values cited in the detailed botanical description which accurately describe the colors of the new *Cephalanthus* plant.

The photograph on the first sheet (FIG. 1) is a side perspective view of a typical flowering plant of 'SMCBM'.

Figure 2:
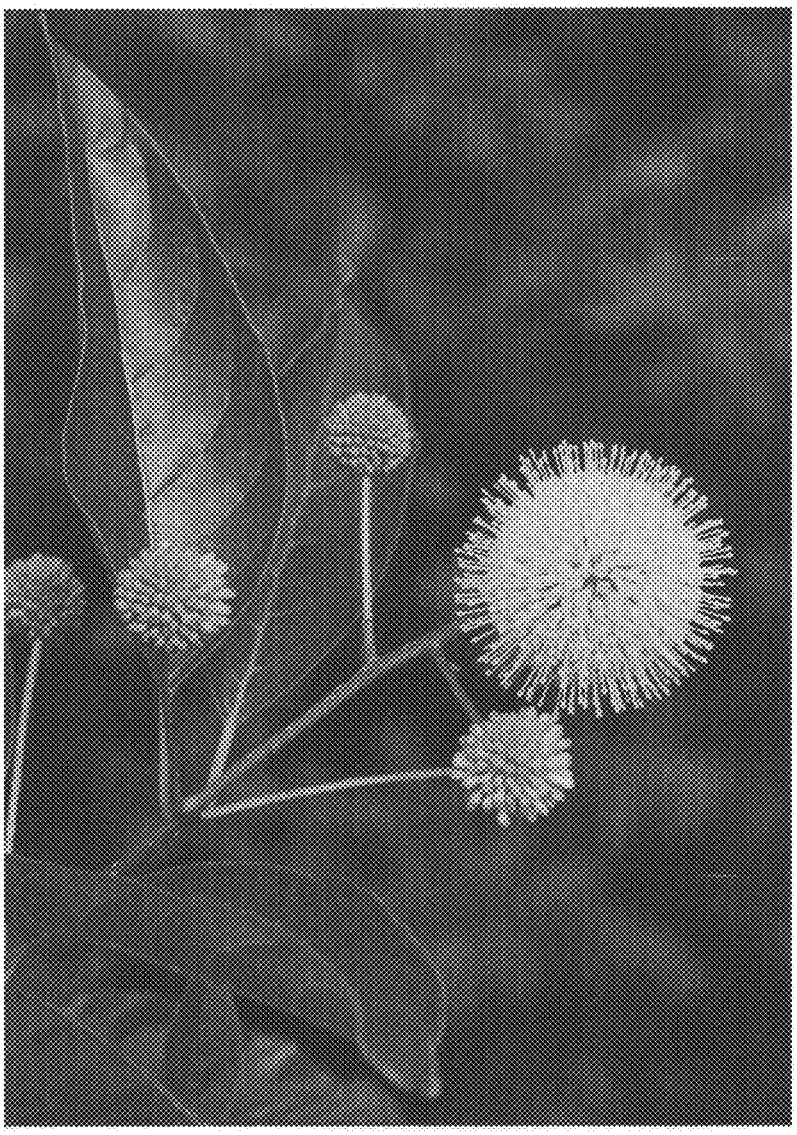

The photograph on the second sheet (FIG. 2) is a close-up view of typical developing and developed inflorescences and leaves of 'SMCBM'.

Figure 3:
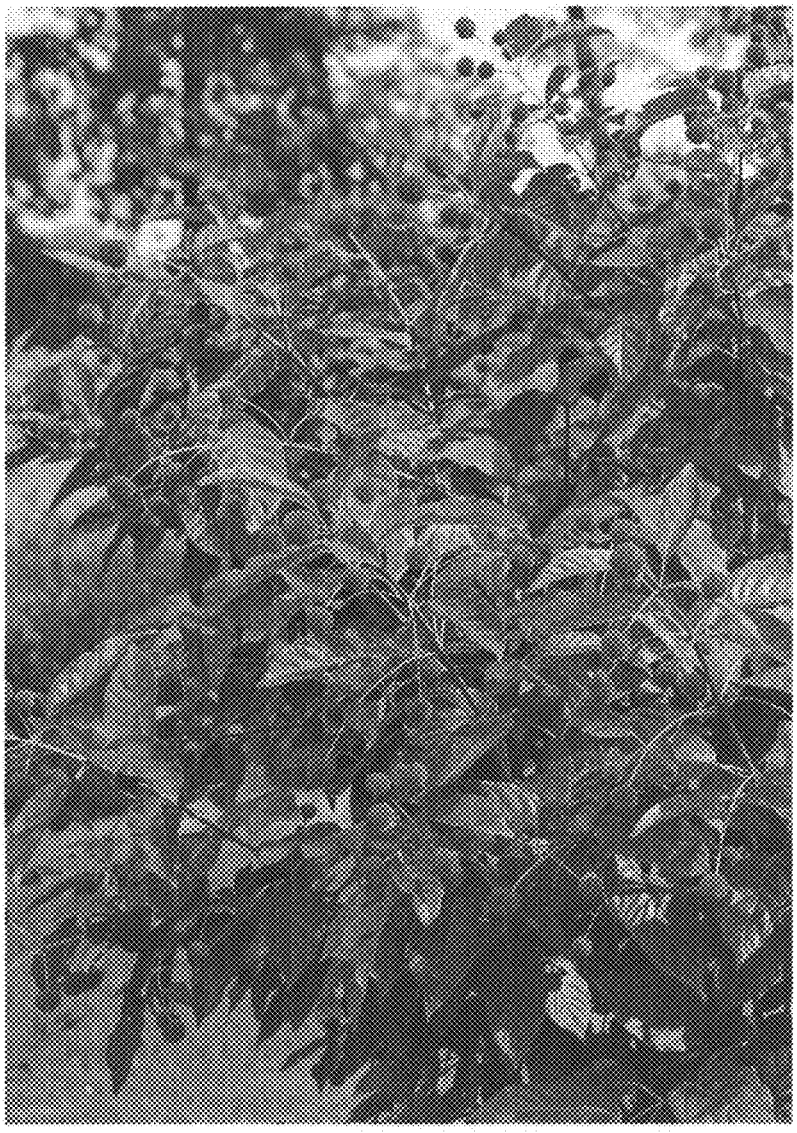

The photograph on the third sheet (FIG. 3) is a side perspective view of a typical plant of 'SMCBM' with mature fruits.

Figure 4:
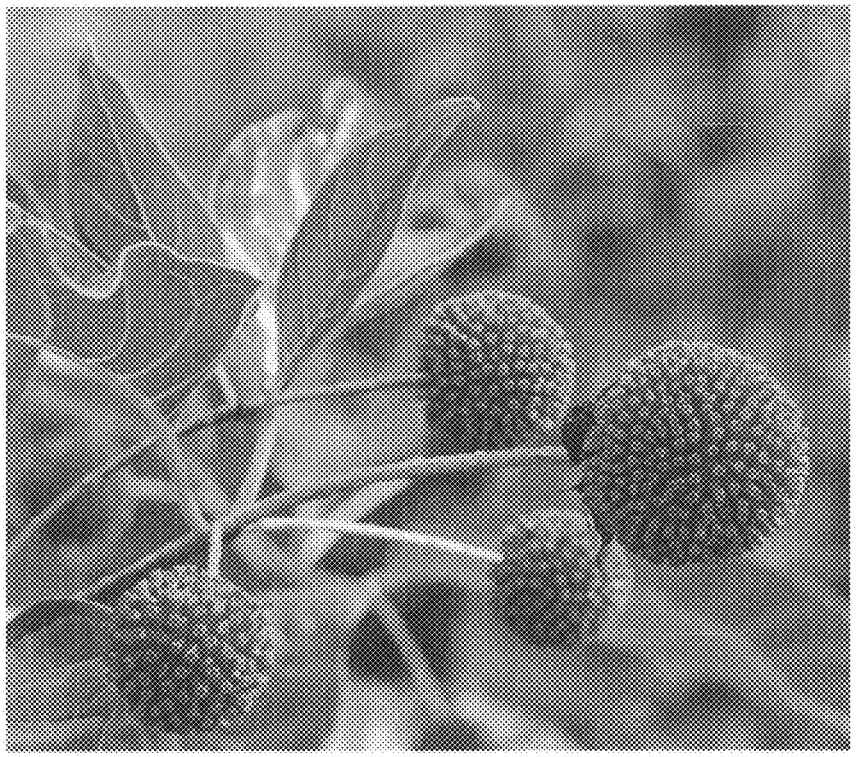

The photograph on the fourth sheet (FIG. 4) is a close-up view of typical developed fruits and leaves of 'SMCBM'.

Plants used for the photographs were grown during the mid to late summer in ground beds in an outdoor nursery in Grand Haven, Mich. and under cultural practices typical of commercial production. Plants were about four years old when the photographs were taken.

DETAILED BOTANICAL DESCRIPTION

The following observations, measurements and values describe plants grown during the summer and autumn in three-gallon containers in a polyethylene-covered greenhouse in Grand Haven, Mich. and under cultural practices typical of commercial production. During the production of the plants, day temperatures ranged from 18° C. to 27° C. and night temperatures ranged from 5° C. to 10° C. Plants were about three years old when the description was taken. In the description, color references are made to The Royal Horticultural Society Colour Chart, 2015 Edition, except where general terms of ordinary dictionary significance are used.

Botanical classification: *Cephalanthus occidentalis* 'SMCBM'.

Parentage:

*Female, or seed, parent.*—*Cephalanthus occidentalis* 'Sugar Shack', not patented.

*Male, or pollen, parent.*—Unknown selection of *Cephalanthus occidentalis*, not patented.

Propagation:

*Type.*—By softwood cuttings.

*Time to initiate roots, summer.*—About one month at temperatures ranging from 18° C. to 27° C.

*Time to produce a rooted young plant, summer.*—About eight months at temperatures ranging from 18° C. to 27° C.

*Root description.*—Medium in thickness; fibrous; typically white to brown in color, actual color of the roots is dependent on substrate composition, water quality, fertilizer, substrate temperature and physiological age of roots.

*Rooting habit.*—Freely branching; dense.

Plant description:

*Plant and growth habit.*—Perennial shrub; upright and mounded plant habit; moderately vigorous growth habit and moderate growth rate.

*Branching habit.*—Freely branching habit with about nine primary lateral branches developing per plant.

*Plant height.*—About 57 cm.

*Plant diameter* (*area of spread*).—About 53 cm.

Lateral branch description:

*Length.*—About 30 cm.

*Diameter.*—About 3 mm.

*Internode length.*—About 5 cm.

*Strength.*—Moderately strong.

*Aspect.*—Erect to about 45° from vertical.

*Texture.*—Smooth, glabrous.

*Color, developing.*—Close to 144D becoming closer to 180B.

*Color, fully developed.*—Close to 201D.

Leaf description:

*Arrangement.*—Opposite, simple.

*Length.*—About 11 cm.

*Width.*—About 5.5 cm.

*Shape.*—Elliptic.

*Apex.*—Cuspidate.

*Base.*—Attenuate.

*Margin.*—Entire.

*Texture and luster, upper surface.*—Smooth, glabrous; glossy.

*Texture and luster, lower surface.*—Slightly rough with sparse pubescent along veins; slightly glossy.

*Venation pattern.*—Pinnate.

*Color.*—Developing leaves, upper surface: Close to 138A; in the autumn, close to N144A to N144C. Developing leaves, lower surface: Close to 138A; in the autumn, close to 151A. Fully expanded leaves, upper surface: Close to 138A; venation, close to 151A; in the autumn, close to 183B and 187A. Fully expanded leaves, lower surface: Close to 138A; venation, close to 145D; in the autumn, close to 151D and 183C.

*Petioles.*—Length: About 2 cm. Diameter: About 1.5 mm. Texture, upper and lower surfaces: Slightly pubescent. Color, upper and lower surfaces: Close to 145C.

Flower description:

*Flower appearance and arrangement.*—Single sessile tubular flowers arranged on dense terminal head-type inflorescences; heads spherical in shape; freely flowering habit with more than 100 flowers per inflorescence and more than 10,000 flowers developing per plant during the flowering season; flowers face all directions depending on position on the head.

*Natural flowering season*.—Plants flower during the summer in Michigan; flowers not persistent.

*Fragrance*.—Slightly fragrant; sweet and earthy.

*Inflorescence height*.—About 4 cm.

*Inflorescence diameter*.—About 3.5 cm.

*Flower diameter*.—About 3 mm.

*Flower length* (*height*).—About 1.5 cm.

*Flower buds*.—Length: About 9 mm. Diameter: About 1 mm. Shape: Ovate. Color: Tube, close to NN155B; at the apex, close to 167B.

*Petals*.—Quantity and arrangement: Four petals fused in a single fine tubular whorl. Length: About 1 mm. Width: About 1 mm. Shape: Oval. Apex: Acute. Margin: Entire. Texture, upper and lower surfaces: Smooth, glabrous. Color: When opening, upper and lower surfaces: Close to NN155A. Fully opened, upper and lower surfaces: Close to NN155A; color becoming closer to 180A with development.

*Sepals*.—Quantity and arrangement: If present, about four or five in a single whorl. Length: About 0.5 mm. Width: About 0.5 mm. Shape: Lanceolate. Apex: Acute. Base: Cuneate. Margin: Entire. Texture, upper and lower surfaces: Smooth, glabrous. Color, upper and lower surfaces: Close to 144C.

*Peduncles*.—Length: About 3 cm to 4 cm. Diameter: About 1.5 mm. Strength: Strong. Aspect: Erect to about 45° from the stem axis. Texture: Smooth, glabrous. Color: Close to 144B variably tinged with close to 168B.

*Reproductive organs*.—Androecium: Quantity per flower: About four. Filament length: About 5 mm. Filament color: Close to NN155D. Anther length: About 1 mm. Anther shape: Globular. Anther color: Close to 200A. Amount of pollen: Abundant. Pollen color: Close to 8A. Gynoecium: Quantity per flower: One. Pistil length: About 1.5 cm. Style length: About 1.5 cm. Style color: Close to NN155D. Stigma appearance: Globular. Stigma color: Close to 200D.

*Fruits*.—Height: About 4 cm. Diameter: About 3.5 cm. Shape: Hard, spherical. Color: Close to 179A.

Garden performance: Plants of the new *Cephalanthus* have been observed to have good garden performance and to tolerate rain, wind and temperatures ranging from about −32° C. to about 36° C.

Pathogen & pest tolerance: To date, plants of the new *Cephalanthus* have not been observed to be tolerant to pathogens and pests common to *Cephalanthus* plants.

It is claimed:

1. A new and distinct *Cephalanthus* plant named 'SMCBM' as illustrated and described.

* * * * *